US00PP26833P2

(12) United States Plant Patent
Deng et al.

(10) Patent No.: US PP26,833 P2
(45) Date of Patent: Jun. 14, 2016

(54) ***CALADIUM* PLANT NAMED 'FIESTA'**

(50) Latin Name: *Caladium×hortulanum*
Varietal Denomination: Fiesta

(71) Applicant: Florida Foundation Seed Producers, Inc., Marianna, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/998,661

(22) Filed: Jan. 30, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

U.S. PATENT DOCUMENTS

PP24,327 P3 3/2014 Deng

OTHER PUBLICATIONS

Wilfret, Gary J., Plant U.S. Pat. No. 8,526, Date of Patent: Dec. 28, 1993, Title: *Caladium* Cultivar 'Florida Sweetheart'.

*Primary Examiner* — Keith Robinson
(74) *Attorney, Agent, or Firm* — Christopher & Weisberg, P.A.

(57) ABSTRACT

A new and distinct cultivar of *Caladium* plant named 'Fiesta', characterized by its compact mounding growth habit, fancy-type heart-shaped leaves that have a large white center, multiple red to greyed purple mid and primary veins, netted greyed-purple secondary veins, and bright red coloration along the mid and primary veins, and relatively dwarf plants that are attractive in containers and perform well in sunny landscapes.

6 Drawing Sheets

ACKNOWLEDGMENT OF FEDERAL RESEARCH SUPPORT

This invention was made with government support under FLA-BRA-04162 awarded by the Cooperative State Research, Education, and Extension Service, USDA and under FLA-GCR-005065 awarded by the National Institute of Food and Agriculture, USDA. The government has certain rights in the invention.

Genus and species: *Caladium×hortulanum.*
Cultivar denomination: 'Fiesta'.

CROSS-REFERENCE TO RELATED APPLICATION n/a

BACKGROUND OF THE NEW CULTIVAR

The present invention relates to a new and distinct cultivar of *caladium* plant, botanically known as *Caladium×hortulanum*, commercially referred to as a fancy leaf-type *caladium*, and hereinafter referred to by the name 'Fiesta'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have compact growth habit, numerous leaves, attractive foliage, and exceptional container and landscape performance.

The new *Caladium* cultivar 'Fiesta' originated from a cross between 'Florida Cardinal' (commercial cultivar, not patented) and 'Florida Sweetheart' (U.S. Plant Pat. No. 8,526) that was made in Bradenton, Fla., in spring 2003. The new *Caladium* cultivar 'Fiesta' was discovered and selected by the inventors as a single plant in Wimauma, Fla. in 2005. The *Caladium* cultivar 'Fiesta' has been found to retain its distinctive characteristics through at least nine generations of successive asexual propagations via tuber divisions since 2004.

Plant Breeder's Rights for this cultivar have not been applied for. 'Fiesta' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'Fiesta' as a new and distinct cultivar of *Caladium:*

1. Compact, symmetrical, outwardly arching and rounded plant form;
2. Mounding, dense and bushy growth habit;
3. Multiple heart-shaped leaves that have a white center, red-purple mid veins, numerous greyed-purple primary veins, red purple bleeding along mid and primary veins, and netted green secondary veins throughout the leaf surface; and 4. Attractive plants in containers or sunny or shady landscapes.

The new cultivar 'Fiesta' differs from its female parent, 'Florida Cardinal', in the following characteristics:

1. Plants of the new cultivar are approximately 20% to 40% shorter than the plants of 'Florida Cardinal';
2. The center area of leaves of the new cultivar is white with red-purple mid and primary veins whereas the center area of leaves of 'Florida Cardinal' is dark red;
3. Leaves of the new cultivar have narrower green margins whereas leaves of 'Florida Cardinal' have wider medium-green margin (up to 3 cm wide);
4. Petioles of mature leaves of the new cultivar are greyed-orange while petioles of mature leaves of 'Florida Cardinal' are greyed-red.

The new cultivar 'Fiesta' differs from its male parent, 'Florida Sweetheart' (U.S. Plant Pat. No. 8,526), in the following characteristics:

1. Leaves of the new cultivar are of the fancy type, heart-shaped, with two large lobes. Whereas leaves of 'Florida Sweetheart' are of the lance type, elongated with a greater leaf length-to-width ratio and small to unobvious lobes;
2. Leaves of the new cultivar are larger and wider than leaves of 'Florida Sweetheart';
3. The center of leaves of the new cultivar is white and red, whereas the center of leaves of 'Florida Sweetheart' is rose;
4. Leaves of the new cultivar are almost flat with thin green margins, while leaves of 'Florida Sweetheart' is undulate with wider margin;
5. The mid and primary veins on leaves of the new cultivar have red-purple bleeding around the veins, whereas the veins on 'Florida Sweetheart' leaves have no surrounding bleeding coloration.

The new *Caladium* cultivar 'Fiesta' can also be compared to the *Caladium* cultivar 'Florida Fantasy', an unpatented commercial cultivar. In side-by-side comparisons of pot-grown plants conducted in Wimauma, Fla., plants of the new *Caladium* cultivar differed from plants of 'Florida Fantasy' *caladium* in the following characteristics:

1. Plants of the new cultivar 'Fiesta' were about 10% to 20% shorter with a more compact growth habit than plants of 'Florida Fantasy';
2. Leaves of the new cultivar 'Fiesta' have broader red purple bleeding coloration by the mid and primary veins whereas leaves of 'Florida Fantasy' have very limited bleeding coloring by the mid and primary veins;
3. Leaf veins of the new cultivar 'Fiesta' have lighter red coloring whereas the leaf veins of 'Florida Fantasy' are darker red;
4. Tubers of the new cultivar can sprout in about 7 to 13 days earlier than tubers of 'Florida Fantasy'.

The new *Caladium* cultivar 'Fiesta' can also be compared to the *Caladium* cultivar 'White Queen', an unpatented, old commercial cultivar. In side-by-side comparisons of pot-grown plants conducted in Wimauma, Fla., plants of the new *Caladium* cultivar differed from plants of 'White Queen' *caladium* in the following characteristics:

1. Plants of the new cultivar 'Fiesta' were about 30% to 40% shorter with a more compact growth habit than plants of 'White Queen';
2. Plants of the new cultivar 'Fiesta' forced from tubers in containers produce approximately 1 to 2-fold more leaves than plants of 'White Queen';
3. The background color of leaves of the new cultivar is whiter and more attractive than the background color of leaves of 'White Queen'. Leaves of 'White Queen' are tinted with much more green;
4. Pot-grown plants of the new cultivar are of higher plant quality than the pot-grown plants of 'White Queen';
5. Tubers of the new cultivar can sprout in about 7 to 12 days earlier than tubers of 'White Queen', and tubers of the new cultivar can produce finished pot plants earlier than tubers of 'White Queen'.

The new *Caladium* cultivar 'Fiesta' can also be compared to the *Caladium* cultivar 'UF-48-5', a patented cultivar (U.S. Plant Pat. No. 24,327). In side-by-side comparisons conducted in Wimauma, Fla., plants of the new *Caladium* cultivar differed from plants of 'UF-48-5' *caladium* in the following characteristics:

1. Plants of the new cultivar 'Fiesta' were about 20% to 30% shorter with a dwarf growth habit than plants of 'UF-48-5' *caladium;*
2. Leaves of the new cultivar 'Fiesta' have deeper red mid and primary veins while leaves of 'UF-48-5' *caladium* have lighter red to pink mid and primary veins;
3. Leaves of the new cultivar 'Fiesta' have more restricted color bleeding by mid and primary veins than leaves of 'UF-48-5' *caladium;*
4. Leaves of the new cultivar 'Fiesta' do not have white blotches between primary veins whereas leaves of 'UF-48-5' have white blotches between primary veins.

DESCRIPTION OF THE FIGURES

The accompanying photographs (as shown in FIGS. 1-6) illustrate the overall appearance of the new *Caladium* cultivar. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
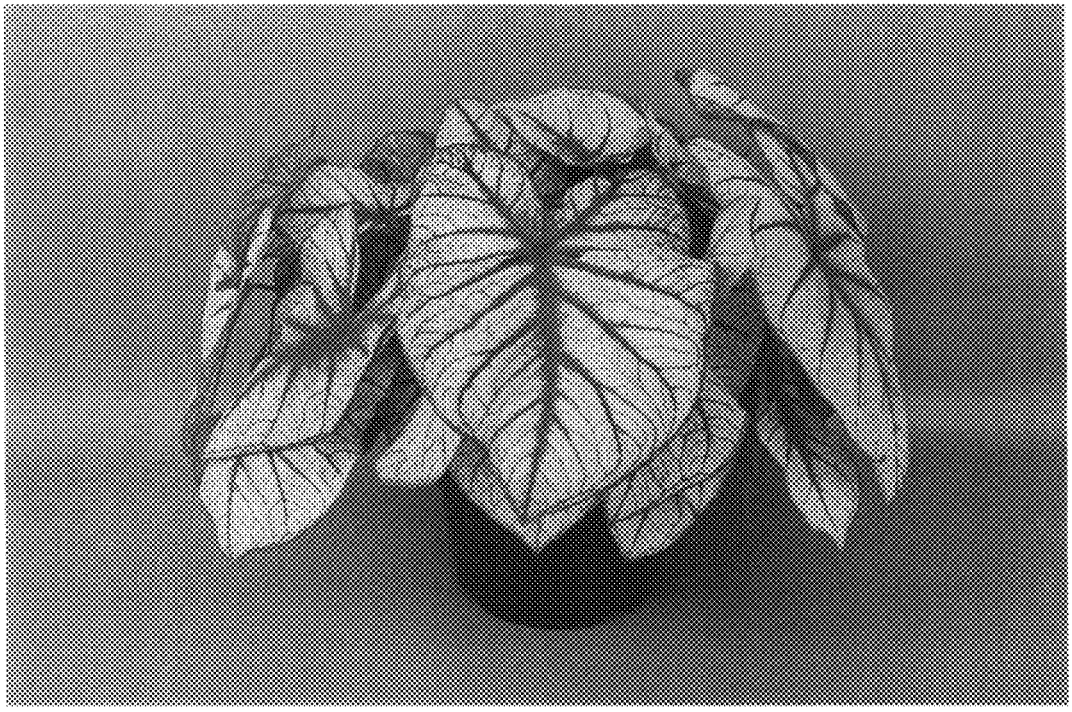
FIG. 1 shows a photograph of a side view of a typical plant (approximately 7-week-old) of the new *Caladium* cultivar 'Fiesta' forced from four No.1-sized tubers (3.8 to 6.4 cm diameter) and grown in a 20.3-cm diameter container in a shadehouse.
Figure 2:
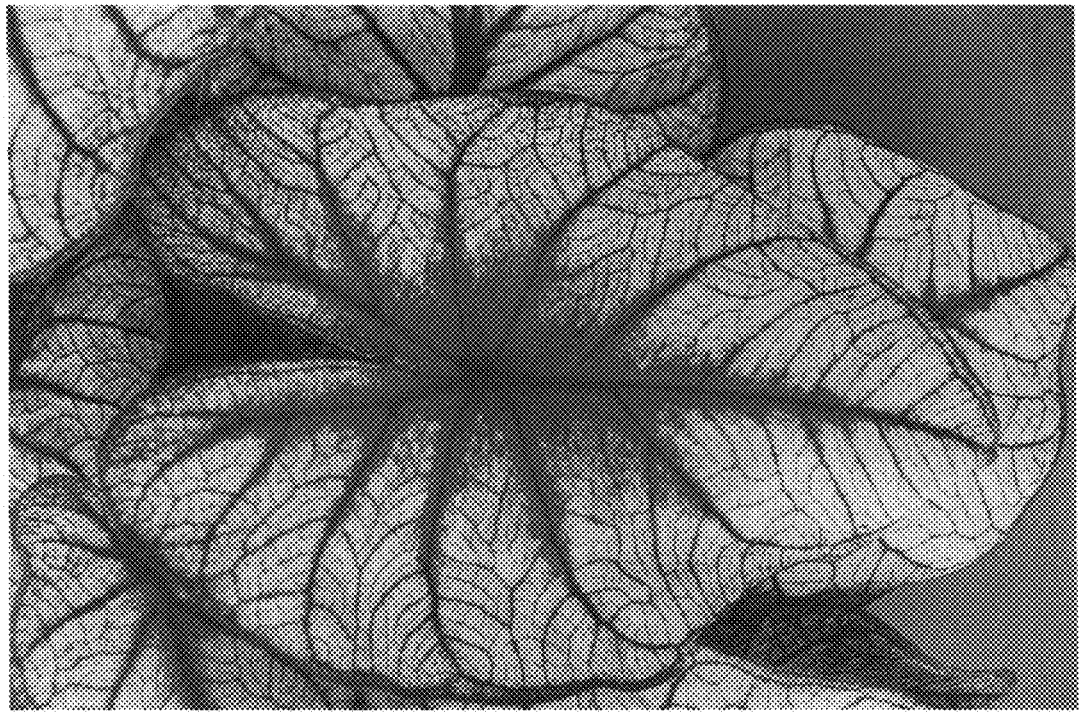
FIG. 2 shows a photograph of a top view of a typical leaf of the new *Caladium* cultivar 'Fiesta' forced from four No.1-sized tubers (3.8 to 6.4 cm diameter) and grown in a 20.3-cm diameter container.
Figure 3:
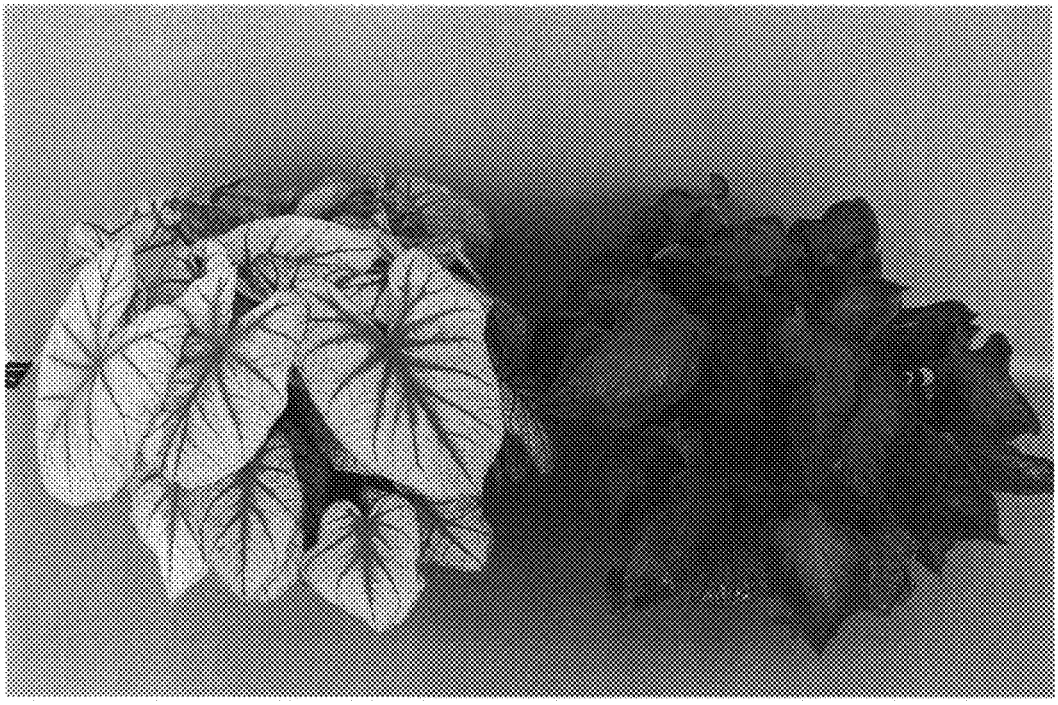
FIG. 3 shows a photograph of a side view of typical plants of 'Fiesta' (left) and 'Florida Sweetheart' *caladium* (right) grown in 20.3-cm diameter container in a shadehouse.
Figure 4:
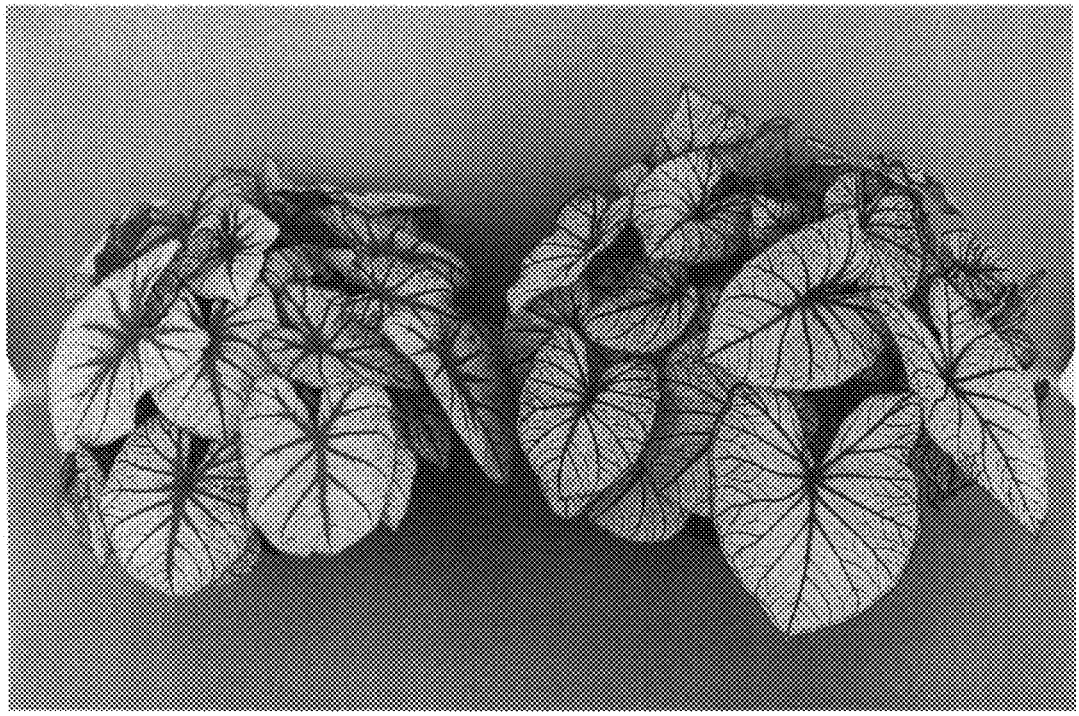
FIG. 4 shows a photograph of a side view of typical plants of 'Fiesta' (left) and 'Florida Fantasy' *caladium* (right) grown in 20.3-cm diameter container in a shadehouse.
Figure 5:
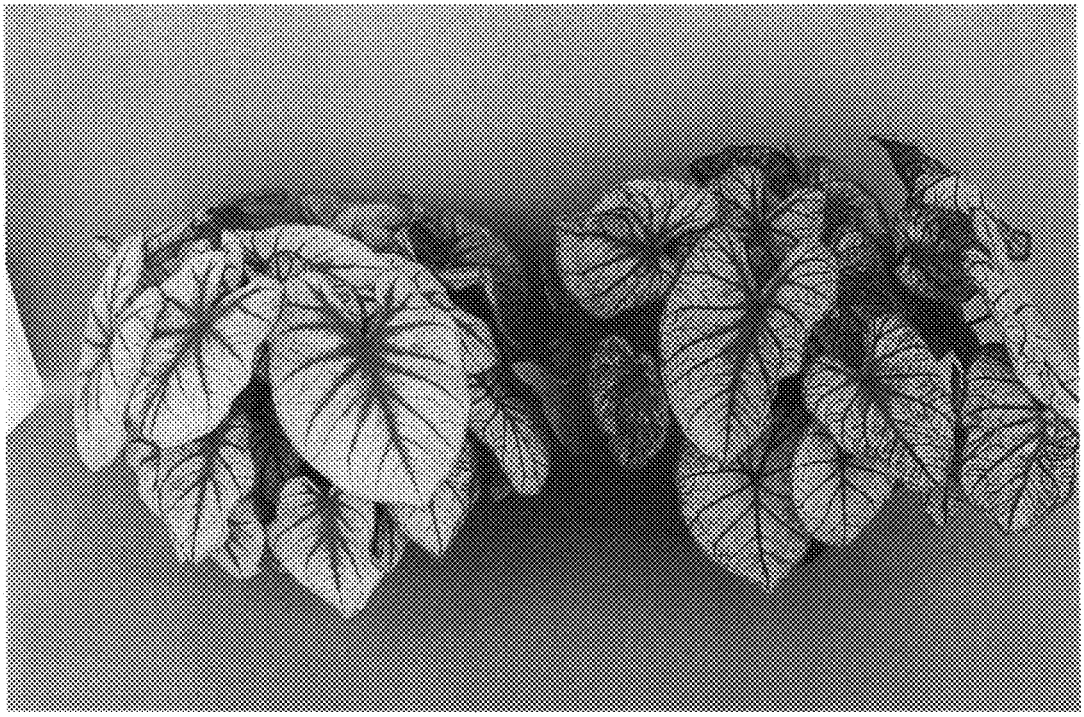
FIG. 5 shows a photograph of a side view of typical plants of 'Fiesta' (left) and 'White Queen' *caladium* (right) grown in 20.3-cm diameter container in a shadehouse.
Figure 6:
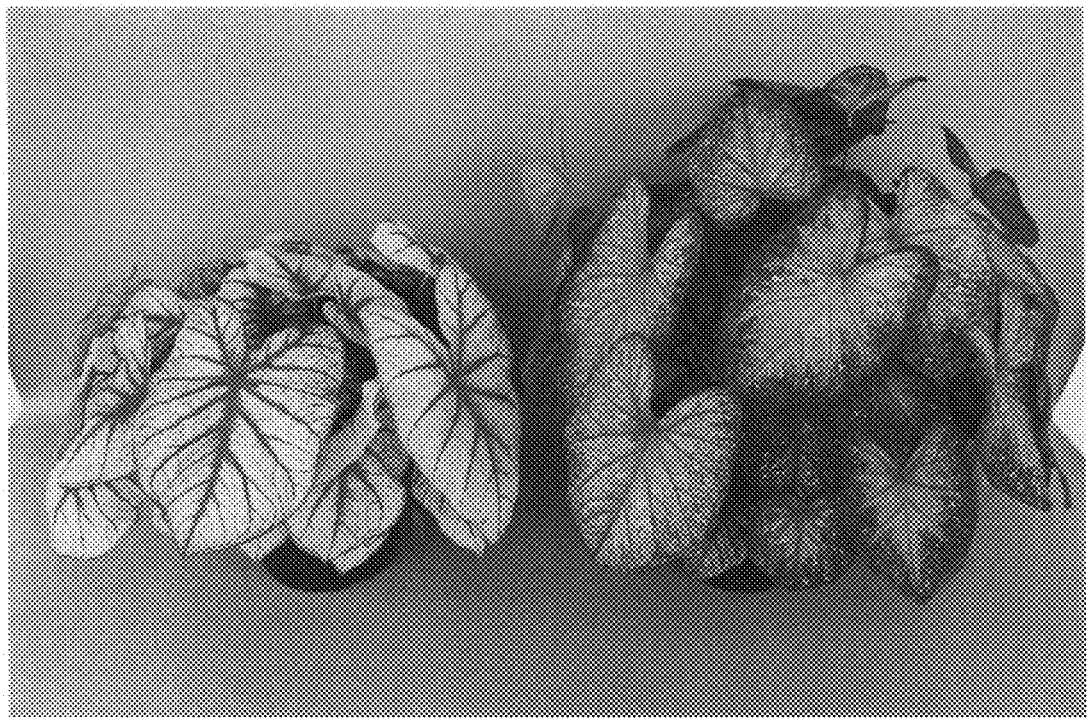
FIG. 6 shows a photograph of a side view of typical plants of 'Fiesta' (left) and 'UF-48-5' *caladium* (right) grown in 20.3-cm diameter container in a shadehouse.

In the following description, color references are made to The Royal Horticultural Society (R.H.S.) Colour Chart, 1986 Edition, except where general terms of ordinary dictionary significance are used. The features of 'Fiesta' described herein are shown in FIGS. 1-6.

Description of Growing Conditions

The following observations and measurements describe plants grown in 20.3-cm containers in Wimauma, Fla., during the summer in a polypropylene-covered shadehouse. All plants were grown under conditions and practices similar to those generally used in commercial *Caladium* production.

During the production of the plants, day temperatures ranged from approximately 75° F. to 92° F., night temperatures ranged from approximately 66.5° F. to 76.1° F., and the light level was approximately 30% reduced in the shadehouse. Plants grown in the shadehouse were approximately seven weeks from planting tubers when the photographs and the detailed description were taken.

Botanical Description

Botanical classification:

*Family*.—Araceae.

*Botanical name*.—*Caladium×hortulanum*.

*Common name*.—*Caladium*.

*Cultivar*.—'Fiesta' (*Caladium×hortulanum* cultivar 'Fiesta').

Parentage:

*Female or seed parent*.—'Florida Cardinal'.

*Male or pollen parent*.—'Florida Sweetheart' (U.S. Plant Pat. No. 8,526).

Propagation:

*Type*.—By tubers and by tuber divisions.

*Time to initiate roots, summer*.—Approximately seven to ten days at 32° C.

*Time to initiate roots, winter*.—Approximately two to three weeks at 24° C.

Tuber description: Jumbo-sized (6.4 to 8.9 cm in diameter) tubers are multi-segmented, bearing six to nine dominant buds.

*Height of tubers*.—2 to 3 cm.

*Diameter of tubers*.—5.7 to 8.2 cm.

*Texture*.—Thick, starchy inside; slightly brittle between tuber segments.

*Color*.—Epidermis, close to brown (RHS 200C); interior, yellow (RHS 10A).

*Root description*.—Dense, thick and white (RHS 155D) fleshy roots.

Plant description:

*Type*.—Herbaceous perennial.

*Plant form*.—Upright, outwardly arching and symmetrical plant.

*Growth habit*.—Compact and mounding, dense foliage, suitable for containers of 10.0 cm or larger diameters or garden beds. Leaf petioles arising from tubers; petioles mostly semi-upright and curving outwardly with development.

*Plant height, from soil level to top of leaf plane, shadehouse-grown plants*.—Approximately 23 cm.

*Plant height, from soil level to top of inflorescences, shadehouse-grown plants*.—Approximately 26 cm.

*Plant spread, shadehouse-grown plants*.—Approximately 42 cm×50 cm.

Foliage description (shadehouse-grown):

*Length, shadehouse-grown plants*.—Approximately 18.7 cm.

*Width, shadehouse-grown plants (flattened)*.—Approximately 13.6 cm.

*Shape*.—Ovate.

*Apex*.—Acuminate to acute.

*Base*.—Cordate.

*Margin*.—Entire.

*Texture, upper surface*.—Smooth, glabrous.

*Texture, lower surface*.—Smooth, glabrous; glaucous.

*Venation pattern*.—Pinnate.

Leaf color (shadehouse-grown plants):

*Fully expanded leaves*.—Upper surface: Center: Close to while (RHS 155C) with bleeding of red-purple (RHS 60C) surrounding the midrib and primary veins. Netted veins of green (RHS 137A and 137B) appear throughout the leaf surface. Border and margins: A narrow line close to green (RHS 137A). Basal notch: Close to greyed-purple (RHS 187B). Venation: Midrib: Close to red-purple (RHS 59A). Primary: Close to greyed-purple (RHS 183C) that changes into green (RHS 137A) toward the margins. Lower surface: Center: Close to greyed-green (RHS 191B) with bleeding of greyed-purple (RHS 185C) and blotching of yellow-white (RHS 155B). Netted veins of greyed-green (RHS 191A) throughout the underside. A line of greyed-purple (RHS 185B) runs from the basal notch to the sinus cavity. Border and margins: Close to greyed-green (RHS 191A). Venation: Midrib: Close to yellow-white (RHS 158D). Primary veins: Close to greyed-green (RHS 195D) with a narrow line of greyed-green (RHS 191A) running down the center of the vein.

Petiole:

*Aspect*.—Mostly erect, curving outwardly with development.

*Length, shadehouse-grown plants*.—Approximately 17 to 21 cm.

*Diameter, distal, shadehouse-grown plants*.—Approximately 3.6 mm.

*Diameter, proximal, shadehouse-grown plants*.—Approximately 6.7 mm.

*Strength*.—Strong, flexible.

*Color, shadehouse-grown plants*.—Close to greyed-orange (RHS 164D) with speckling or streaks of greyed-orange (RHS165A).

*Wing length, shadehouse-grown plants*.—Approximately 3.0 cm to 4.8 cm.

*Wing diameter, shadehouse-grown plants*.—Approximately 4.4 mm to 8.4 mm.

*Wing color, shadehouse-grown plants*.—Close to orange-white (RHS 159C) with blotching of greyed-orange (RHS 165A).

Inflorescence description: Plants of 'Fiesta' produce inflorescences only occasionally.

*Inflorescence arrangement*.—Upright hooded spathe surrounding a columnar spadix borne on an upright scape. Spadix carries sessile, simple female and male flowers separated into two zones. Female flowers arranged on the lower one-third of the spadix; male flowers arranged on the upper two-thirds of the spadix. Sterile flowers develop between female and male flower zones. Spadix constricts near the sterile flower zone.

*Fragrance*.—None detected.

*Natural flowering season/longevity*.—Plants of 'Fiesta' may flower in spring or early summer in central Florida. Flowers develop about seven weeks after growth commence. Inflorescences last about four days before fading.

*Spathe*.—Length: Approximately 10.0 cm. Width: Distal: Approximately 2.3 cm. Proximal: Approximately 2.1 cm. Shape: Ovate to somewhat obovate. Apex: Acute to acuminate. Base: Tapering. Margin: Entire. Texture: Upper and lower surfaces: Smooth, glabrous. Color: Front surface: Upper two-thirds: Close to yellow-white (RHS 158C). Lower one-third: Close to green (RHS 143C). Rear surface: Upper two-thirds: Close to yellow-white (RHS 158C). Lower one-third: Close to green (RHS 143C) with streaks of yellow-green (RIIS 145D).

*Spadix*.—Length, entire spadix: Approximately 10.0 cm. Length, male flower zone: Approximately 4.0 cm. Length, sterile flower zone: Approximately 1.8 cm. Length, female flower zone: Approximately 1.9 cm. Diameter, male flower zone: Approximately 9 mm. Diameter, sterile flower zone: Approximately 6 mm. Diameter, female flower zone: Approximately 9.5 mm. Shape: Spindle-shaped to columnar. Apex: Obtuse. Base: Obtuse. Aspect: Upright. Color, mature, male zone: Close to yellow-white (RHS 158B). Color, mature, sterile zone: Close to yellow (RHS 155B). Color, mature, female zone: Close to greyed-orange (RHS 164C). Male flowers: Quantity per spadix: Approximately 155. Shape: Obovate. Height: Approximately 3.6 mm. Diameter: Approximately 2.2 mm. Color of pollen: Close to yellow (RHS 10B). Amount of pollen: Scant. Female flowers: Quantity per spadix: Approximately 166. Shape: Obovate. Height: Approximately 1.6 mm. Diameter: Approximately 1.3 mm.

*Scape*.—Length: Approximately 21 cm. Diameter: Approximately 5.5 mm. Strength: Sturdy, flexible. Aspect: Erect, Upright, but with some arching. Texture: Smooth, glabrous, glaucous. Color, proximal: Close to yellow-green (RHS 144B) with streaks of yellow-green (RHS 144A). Just below spathe: Close to green (RHS 144A).

*Seed and fruit*.—Seed and fruit development has not been observed on inflorescences that were not hand-pollinated.

Disease/pest resistance: Plants of 'Fiesta' have been observed to have a good level of resistance to *Xanthomonas* leaf spot.

Temperature tolerance: Tolerant to temperatures ranging from approximately 7° C. to approximately 40° C.

Sunburn tolerance: High levels of tolerance to sunburns.

Comparison with Known Cultivars

The new cultivar 'Fiesta' was evaluated for tuber production at the Gulf Coast Research and Education Center in Wimauma, Fla. in 2007 and 2009. The soil was EauGallie fine sand with about 1% organic matter and a pH value between 6.2 and 7.4. *Caladium* plants were grown in the field using a plastic-mulched raised-bed system. For the 2007 evaluation, ground beds (81 cm wide, 20 cm high) were fumigated on 3 April with a mixture of 67% methyl bromide and 33% chloropicrin (by volume) at the rate of 196 $kg \cdot ha^{-1}$. *Caladium* seed pieces (tuber pieces, approximately 2.5×2.5×2.5 cm) were planted manually on 26 April with approximately 25.4 cm between-row spacing and approximately 15.2 cm in-row spacing. Drip tapes were buried under the plastic mulch and delivered approximately 6 mm of water to the bed per day. Fertigation (through the drip irrigation system) began when young *caladium* plants emerged from the soil, supplying soluble fertilizer (6N-0.8P-3.9K) at the rate of approximately 1.9 kg of $nitrogen \cdot ha^{-1} \cdot day^{-1}$ and a total 290 kg of $nitrogen \cdot ha^{-1}$ per growing season. Tubers (new crop) were dug, washed, and dried in early January 2008. Dried tubers from each experimental field plot were weighed, graded, and counted in late January 2008. Tuber grading was by the tuber maximum diameter: Super Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a Production Index (PI) to show the relative economic value of the harvested tubers per field plot: PI=8n(Supper Mammoth)+6n(Mammoth)+4n(Jumbo)+2n(No.1)+1n(No.2), where n=number of tubers in the grade. The relative values assigned to the five tuber grades in calculating PIs were based on the relative market prices provided by Florida *caladium* tuber producers.

For the 2009 evaluation, beds were fumigated on 27 February with a mixture of 50% methyl bromide and 50% chloropicrin (by volume) at the rate of 196 $kg \cdot ha^{-1}$. *Caladium* seed pieces were planted on 9 Apr. 2009 at approximately 15-cm spacing between rows and in rows. The irrigation and fertigation system was the same as the one used in 2007, but one teaspoon (approximately seven grams) of OSMOCOTE® controlled-release fertilizer (15N-2.6P-10K, 5-6 months) was applied to each plant on 21 July. Tubers were dug from 30 Nov. to 2 Dec. 2009, followed by washing, drying, weighing, grading, and counting as was done in 2007.

Field plots were arranged each season in three randomized complete blocks, and each plot (1.2 $m^2$) was planted with 30 *caladium* seed pieces. Two commercial cultivars, 'Florida Fantasy' and 'White Queen', were included as controls in each block. Analyses of variance were conducted using the PROC GLM procedure in SAS (SAS Institute, Cary, N.C.) to compare the tuber yields of 'Fiesta' to that of 'Florida Fantasy' and 'White Queen'.

Table 1 shows the tuber weight, marketable tubers, production index, and grade distribution of the new cultivar 'Fiesta' grown in Wimauma, Fla. in 2007 and 2009, as compared to those of 'Florida Fantasy' and 'White Queen'. Values presented for each year are means of three plots in three randomized complete blocks.

TABLE 1

| Cultivars | Tuber | | |
|---|---|---|---|
| | Weight (kg) | Marketable (no.) | Production index[z] |
| | Year 2007 | | |
| Fiesta | 8.2 ns | 59.0 ns | 221.0 ns |
| Florida Fantasy | 4.2 ns | 52.1 ns | 142.2 ns |
| White Queen | 4.7 ns | 50.9 ns | 166.4 ns |
| | Year 2009 | | |
| Fiesta | 2.6 ns | 26.3 ns | 80.3 ns |
| Florida Fantasy | 2.3 ns | 27.0 ns | 69.3 ns |
| White Queen | 2.3 ns | 20.3 ns | 64.0 ns |

| Cultivars | Tuber grade distribution (%) | | | | |
|---|---|---|---|---|---|
| | Super Mammoth | Mammoth | Jumbo | No. 1 | No. 2 |
| | Year 2007 | | | | |
| Fiesta | 6.6 a[y] | 21.5 ns | 27.8 ns | 31.3 ns | 12.9 ns |
| Florida Fantasy | 1.9 b | 9.4 ns | 23.4 ns | 41.4 ns | 24.0 ns |
| White Queen | 0.6 b | 12.4 ns | 41.9 ns | 33.9 ns | 11.3 ns |

TABLE 1-continued

| | Year 2009 | | | | |
|---|---|---|---|---|---|
| Fiesta | 0 ns | 13.9 ns | 36.7 ns | 25.4 b | 24.0 ns |
| Florida Fantasy | 0 ns | 8.9 ns | 23.5 ns | 42.1 a | 25.5 ns |
| White Queen | 1.7 ns | 10.3 ns | 38.6 ns | 36.5 ab | 13.0 ns |

[z]The production index is an indicator of economic value of the crop harvested and is calculated as: N (No.2s) + 2N (No. 1s) + 4N (Jumbos) + 6N (Mammoth) + 8N (Super Mammoth); where N = number of tubers in each grade. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth ( >11.4 cm).
[y]Mean values with the same letters within columns are not significantly different at P ≤ 0.05.
ns: not significantly different at P < 0.05.

As shown in Table 1, the tuber weight, marketable number of tubers, and production indexes of the new cultivar 'Fiesta' were not significantly different from those of 'Florida Fantasy' and 'White Queen' in 2007 and 2009: tubers per plot weighed between 4.2 and 8.2 kg in 2007 and between 2.3 and 2.6 kg in 2009; number of marketable tubers was between 50.9 and 59.0 in 2007 and between 20.3 and 27.0 in 2009; production indexes were between 142.2 and 221.0 in 2007 and between 64.0 and 80.3 in 2009. The tuber size distribution of 'Fiesta', 'Florida Fantasy', and 'White Queen' was also not significantly different, except that 'Florida Fantasy' produced more No. 1-grade tubers than 'Fiesta'.

Table 2 shows a comparison of the plant height, number of leaves, leaf length, and leaf width of the new cultivar 'Fiesta' with 'Florida Fantasy', and 'White Queen', approximately 4 months after planting 2.54-cm tuber pieces (propagules) in ground beds in full sun in 2007 and 2009. Values presented are means of data from three replications and three plants measured per plot per year over two years.

TABLE 2

| Cultivars | Plant height (cm) | Leaves (no.) | Leaf length[z] (cm) | Leaf width[y] (cm) |
|---|---|---|---|---|
| Fiesta | 31.9 ns | 22.0 a | 22.4 b | 17.6 ns |
| Florida Fantasy | 38.3 ns | 21.5 a | 28.7 a | 18.0 ns |
| White Queen | 34.8 ns | 13.6 b | 28.9 a | 18.3 ns |

[z]Leaf length was measured on the largest leaves along the longest line from the leaf lobe to the leaf tip.
[y]Leaf width was measured on the largest leaves across the widest middle part.
[x]Mean values with the same letters within columns are not significantly different at P ≤ 0.05.
ns: not significantly different at P ≤ 0.05.

As shown in Table 2, Plants of the new cultivar 'Fiesta' and 'Florida Fantasy' had similar numbers of leaves per plant (22.0 and 21.5). Their leaves were similar in width (17.6 and 18.0 cm), but had different lengths (22.4 cm and 28.7 cm, respectively). Compared to plants of 'White Queen', plants of 'Fiesta' had 63% more leaves and leaves were 6.5 cm shorter.

Table 3 shows the landscape performance of the new cultivar 'Fiesta' with 'Florida Fantasy' and 'White Queen' when planted in ground beds in full sun in 2007 and 2009. Values presented are means of three replications in each year.

Landscape performance was evaluated on the same plots used for evaluating tuber production. A scale of 1 to 5 was used with 1 being very poor (few leaves and lack of vigor), and 5 being excellent (full plants, numerous leaves, and bright color display). Leaf sun tolerance was evaluated on a scale of 1 to 5, with 1 being very susceptible to sunburn (leaves having numerous sun-dainaged areas or holes) and 5 being resistant to sunburn (no visible sun-damaged areas). Three to four evaluations were conducted in each growing season for plant performance and sunburn tolerance. Evaluations were done in July, August, and September 2007, and August, September, and October in 2009.

TABLE 3

| | 2007 | | | 2009 | | |
|---|---|---|---|---|---|---|
| Cultivars | July | August | September | August | September | October |
| Fiesta | 4.1[z] a | 3.3 ns | 2.7 ns | 3.2 ns | 4.3 ns | 4.2 ns |
| Florida Fantasy | 2.9 b | 3.4 ns | 3.1 ns | 3.7 ns | 4.3 ns | 4.2 ns |
| White Queen | 3.3 ab | 3.5 ns | 3.6 ns | 3.2 ns | 3.8 ns | 3.8 ns |

[z]Plants were rated on a scale of 1 to 5, with 1 being very poor, 3 fair and acceptable, and 5 being excellent in plant vigor, fullness, and color display, on 27 July, 28 August, and 15 September 2007, and 12 August, 15 September, and 8 October 2009. Mean values with the same letters within columns are not significantly different at P ≤ 0.05.
NS: Not significantly different at P ≤ 0.05.

As shown in Table 3, plants of 'Fiesta', 'Florida Fantasy', and 'White Queen' performed similarly in both 2007 and 2009 growing seasons, with similar performance ratings (2.7 to 4.3) in two of the three evaluations in 2007 and in all three evaluations in 2009. In one evaluation (July 2007), 'Fiesta' received a higher rating (4.1) than 'Florida Fantasy' (2.9).

Table 4 shows the leaf sunburn tolerance of 'Fiesta' with 'Florida Fantasy' and 'White Queen' when tuber pieces were planted in ground beds and plants were grown in full sun in 2007 and 2009. Values presented arc means of three replications in each year.

Leaf sun burn tolerance was evaluated on a scale of 1 to 5, with 1 being very susceptible to sun burns (leaves having numerous sun-damaged areas or holes) and 5 being resistant to sunburn (no visible sun-damaged areas). A total of nine evaluations were conducted for plant performance over three growing seasons in July, August, and September 2007, and August, September, and October 2009.

TABLE 4

| | 2007 | | | 2009 | | |
|---|---|---|---|---|---|---|
| Cultivars | July | August | September | August | September | October |
| Fiesta | 4.0[z] ns | 4.6 ns | 4.2 ab | 4.3 ns | 4.5 ns | 4.3 ns |
| Florida Fantasy | 3.8 ns | 4.3 ns | 4.0 b | 4.0 ns | 4.5 ns | 3.8 ns |
| White Queen | 3.5 ns | 4.8 ns | 4.6 a | 4.8 ns | 5.0 ns | 4.5 ns |

[z]Plant sunburn tolerance was rated on a scale of 1 to 5, with 1 being very poor, 3 fair and acceptable, and 5 being excellent without showing any signs of leaf burns or holes caused by sunburn on leaf surfaces, on 27 July, 28 August, and 15 September 2007, and 12 August, 15 September, and 8 October 2009.
[y]Mean values with the same letters within columns are not significantly different at P ≤ 0.05.
ns: Not significantly different at P ≤ 0.05.

As shown in Table 4, plants of 'Fiesta' showed excellent sunburn tolerances in both 2007 and 2009 growing seasons, with sunburn tolerance ratings between 4.0 and 4.6 in all six evaluations. Plants of 'Florida Fantasy' and 'White Queen' received similar sunburn tolerance ratings (3.8 to 4.5 for 'Florida Fantasy' and 3.5 to 5.0 for 'White Queen'.

The suitability of 'Fiesta' for pot plant production was evaluated by forcing tubers in 11.4-cm containers in spring 2008. Intact No. 1-sized tubers (>3.8 cm and <6.4 cm in diameter) were planted in a peat/vermiculite mix (VerGro Container Mix A, Verlite, Tampa, Fla.) on 17 Apr. 2008. The study was conducted in a greenhouse with 45% light exclusion. Average daily temperatures in the greenhouse ranged from a low of 16° C. at night to 29° C. during the day during the experiment. Potted plants were arranged on metal benches in the greenhouse in a randomized complete block design with eight replications. Plant height, plant width, number of leaves, and foliar characteristics were recorded on 12 Jun. 2008, 8 weeks after planting. Quality of the potted *Caladium* plants was rated on a scale of 1 to 5, 1=very poor, few leaves, totally unacceptable as potted plants, and 5=very attractive, with many bright, colorful leaves, a full plant, a symmetrical shape, and an appropriate height.

Table 5 shows a comparison of number of days to sprout, plant height, plant width, leaf number, leaf length, leaf width, and quality rating of 'Fiesta' with 'Florida Fantasy' and 'White Queen' when intact and de-eyed tubers were forced in containers in spring 2008.

TABLE 5

| | Days to sprout[z] | | Plant height (cm) | |
|---|---|---|---|---|
| Cultivars | Intact | De-eye | Intact | De-eye |
| Fiesta | 22 b | 23 b | 20.3 b | 18.6 b |
| Florida Fantasy | 35 a | 30 a | 22.9 b | 21.5 b |
| White Queen | 34 a | 30 a | 32.0 a | 29.1 a |
| | Leaves (no.) | | Leaf length (cm) | |
| Cultivars | Intact | De-eye | Intact | De-eye |
| Fiesta | 14.9 a | 32.8 a | 27.1 ab | 20.3 b |
| Florida Fantasy | 14.4 a | 20.6 b | 24.8 b | 23.0 a |
| White Queen | 8.1 b | 11.4 c | 29.4 a | 23.6 a |
| | Leaf width (cm) | | Quality rating | |
| Cultivars | Intact | De-eye | Intact | De-eye |
| Fiesta | 21.7 a | 14.6 b | 2.4 b | 4.0 a |
| Florida Fantasy | 17.7 b | 16.3 ab | 3.0 a | 3.7 a |
| White Queen | 21.9 a | 18.1 a | 1.9 c | 2.8 b |

[z]Number of days from planting to the first unfurled leaf. Mean separation within column for each cultivar by Fisher's least-significant-difference test at $P \leq 0.05$.

As shown in Table 5, the new cultivar 'Fiesta' was quick to sprout regardless of tuber treatments. Intact and de-eyed tubers sprouted 22 and 23 days after planting, respectively, 7 to 13 days earlier than 'Florida Fantasy' and 'White Queen' (Table 5).

Plants of 'Fiesta' had an average height of 20.3 cm (intact tubers) and 18.6 cm (de-eyed tubers), similar to the plant height of 'Florida Fantasy' (22.9 cm for intact tubers and 21.5 cm for de-eyed tubers), but significantly shorter than the height of 'White Queen' (32.0 cm for intact tubers and 29.1 cm for de-eyed tubers) (Table 5). Plants of 'Fiesta' had an average of 14.9 (for intact tubers) or 32.8 (de-eyed tubers) leaves per plant, 84% and 188% more than 'White Queen' plants had (Table 5). Leaves of 'Fiesta' and 'White Queen' plants from intact tubers were similar in length and width, whereas leaves of 'Fiesta' plants from de-eyed tubers were shorter and narrower than those of 'White Queen' plants from de-eyed tubers. Plants of 'Fiesta' received a quality rating of 2.4 (for intact tubers) and 4.0 (for de-eyed tubers), respectively, which were significantly higher than the quality rating of 'White Queen' plants.

Plants of 'Fiesta' from intact tubers had similar leaf numbers (14.9 and 14.1) and leaf lengths (27.1 and 24.8 cm) with plants of 'Florida Fantasy', but a greater leaf width and a lower quality rating than plants of 'Florida Fantasy'. However, plants of 'Fiesta' from de-eyed tubers had 59% more leaves, and leaves were 2.7 cm shorter and appeared to be 1.7 cm narrower than those leaves of 'Florida Fantasy' from de-eyed tubers. Plant quality ratings of 'Fiesta' and 'Florida Fantasy' were comparable (4.0 and 3.7) when their tubers were de-eyed before planting.

We claim:

1. A new and distinct *Caladium* plant named 'Fiesta' as illustrated and described herein.

* * * * *